United States Patent
Lee et al.

(10) Patent No.: US 10,912,180 B2
(45) Date of Patent: Feb. 2, 2021

(54) X-RAY SOURCE APPARATUS AND CONTROL METHOD THEREOF

(71) Applicant: KOREA UNIVERSITY RESEARCH AND BUSINESS FOUNDATION, Seoul (KR)

(72) Inventors: Cheol Jin Lee, Seoul (KR); Sang Heon Lee, Seoul (KR); Jun Soo Han, Uijeongbu-si (KR); Han Bin Go, Seongnam-si (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 16/371,396

(22) Filed: Apr. 1, 2019

(65) Prior Publication Data
US 2019/0306963 A1    Oct. 3, 2019

(30) Foreign Application Priority Data

Mar. 30, 2018  (KR) .................. 10-2018-0037443
Jan. 10, 2019  (KR) .................. 10-2019-0003152

(51) Int. Cl.
    *H05G 1/02*   (2006.01)
    *H01J 35/06*  (2006.01)
    *H05G 1/34*   (2006.01)

(52) U.S. Cl.
    CPC ............. *H05G 1/02* (2013.01); *H01J 35/06* (2013.01); *H05G 1/34* (2013.01); *H01J 2201/30469* (2013.01)

(58) Field of Classification Search
    CPC ... H05G 1/02; H05G 1/34; H01J 35/06; H01J 2201/30469
    See application file for complete search history.

(56) References Cited

U.S. PATENT DOCUMENTS 7,220,971 B1 *   5/2007  Chang ................... G21K 5/04
                                              250/398
2009/0039754 A1 *  2/2009  Tolt .................... H01J 31/127
                                              313/310
(Continued)

FOREIGN PATENT DOCUMENTS

KR    10-1239395 B1    3/2013
KR    10-1371289 B1    3/2014
(Continued)

OTHER PUBLICATIONS

Dong Hoon Shin et al., "Point-type Carbon Nanotube Field Emitters", Technical Digest, 2015 28th International Vacuum Nanoelectronics Conferemce, Jul. 13-17, 2015, Guangzhou, China.

*Primary Examiner* — David P Porta
*Assistant Examiner* — Mamadou Faye
(74) *Attorney, Agent, or Firm* — Hauptman Ham, LLP

(57) ABSTRACT

The present disclosure relates to an X-ray source apparatus and a control method of the X-ray source apparatus in which a cathode electrode and a gate electrode are arranged in an array form to enable matrix control, and, thus, it is possible to irradiate X-rays at an optimum dose for each position on the subject. Therefore, it is possible to suppress the irradiation of more X-rays than are needed to the subject. Also, it is possible to obtain a high-resolution and high-quality X-ray image. As such, two-dimensional matrix control makes it easy to control the dose of X-rays and makes it possible to uniformly irradiate X-rays to the subject. Therefore, it is possible to manufacture a high-resolution surface X-ray source with less dependence on the size of the focus of electron beams.

16 Claims, 8 Drawing Sheets

(56) References Cited

U.S. PATENT DOCUMENTS

| | | | |
|---|---|---|---|
| 2010/0181896 A1* | 7/2010 | Lee | D06M 10/005 |
| | | | 313/496 |
| 2017/0084417 A1* | 3/2017 | Park | H01J 1/30 |
| 2017/0303874 A1* | 10/2017 | Lee | H05G 1/02 |
| 2018/0323406 A1* | 11/2018 | Li | H01L 51/5296 |
| 2019/0229366 A1* | 7/2019 | Zheng | H01M 10/052 |

FOREIGN PATENT DOCUMENTS

| | | |
|---|---|---|
| KR | 10-2015-0043354 A | 4/2015 |
| KR | 10-2017-0089387 A | 8/2017 |

\* cited by examiner

X-RAY SOURCE APPARATUS AND CONTROL METHOD THEREOF

CROSS-REFERENCE TO RELATED APPLICATION

This application claims the benefit under 35 USC 119(a) of Korean Patent Applications No. 10-2019-0003152 filed on Jan. 10, 2019 and No. 10-2018-0037443 filed on Mar. 30, 2018 in the Korean Intellectual Property Office, the entire disclosures of which are incorporated herein by reference for all purposes.

TECHNICAL FIELD

The present disclosure relates to an X-ray source apparatus and a control method of the X-ray source apparatus in which a cathode electrode and a gate electrode are arranged in an array form to enable matrix control, and, thus, dose can be controlled depending on the position on a subject.

BACKGROUND

Characteristics of an X-ray source are determined by the dose, energy, and focus of X-rays. In order to obtain an X-ray source required for medical or industrial inspection, a high-brightness and high-current electron emitter is needed. In this case, the brightness is measured as characteristics of the electron emitter, and when high-density electrons are emitted in a specific direction, the brightness increases.

In general, a cold cathode X-ray source attracts electron beams from a carbon nanotube electron emitter by applying a voltage to a gate electrode and then focuses the electron beams to high density through a focusing electrode and induces them to an anode electrode. Further, if a high voltage is applied between a cathode electrode and the anode electrode, electrons are accelerated toward the anode electrode and collide with the anode electrode, and, thus, X-rays are generated from the anode electrode.

A conventional X-ray source operates by thermionic emission and uses a reflective anode electrode. Thus, an X-ray is radially emitted from a point light source. Therefore, it is difficult to control the dose of X-rays, and the intensity of X-rays is not uniform.

Further, in the conventional cold cathode electron emitter, a carbon nanotube (CNT) has mainly been used as a material of an electron emitter. The electron emitter has been manufactured by mixing the CNT and a conductive organic material to a paste. While the CNT paste electron emitter is manufactured, the CNT which serves as a field emitter can be contaminated by unwanted organic material, and it is very difficult to achieve vertical orientation of the CNT. Further, the CNT paste electron emitter generates a gas caused by the organic material during field emission, and, thus, the vacuum level in the device decreases, which may cause serious problems such as a sharp decrease in the field emission efficiency and a reduction of the lifetime of the field electron emitter.

Furthermore, in the conventional X-ray source, a thermionic emission-based point light source has been used, and, thus, it is difficult to control the dose of X-rays. Also, X-rays are radially generated, and, thus, the energy of X-rays is not uniform. Further, electron beams colliding with the anode electrode have a large-sized focus, and, thus, there is a limit in increasing the resolution of an X-ray image.

SUMMARY

In view of the foregoing, the present disclosure provides an X-ray source apparatus and a control method of the X-ray source apparatus in which emitters are fabricated using a CNT thin film, a graphene thin film, or a nanocarbon material thin film to increase the field emission efficiency, a transmission-type anode is used to enable X-rays to be emitted in the form of a surface light source to a subject, and electron beams generated from the emitters are driven by matrix control to irradiate X-rays at an optimum dose for each position on the subject.

However, problems to be solved by the present disclosure are not limited to the above-described problems. There may be other problems to be solved by the present disclosure.

According to an aspect of the present disclosure, an X-ray source apparatus that emits X-rays to a subject includes: a plurality of cathode electrodes having one or more emitters formed on an upper surface of a cathode electrode to emit electrons; an anode electrode arranged at a predetermined distance from the cathode electrodes; gate electrodes positioned between the emitters and the anode electrode and formed by transferring a graphene thin film on a metal electrode having at least one or more openings; a focusing lens positioned between the gate electrodes and the anode electrode and configured to focus the electron beams emitted from the emitters on the anode electrode; and a control module configured to adjust the dose of X-rays for each position on the subject by performing two-dimensional matrix control to the emitters and the gate electrodes. Herein, the cathode electrodes are arranged in an array form, the gate electrodes are arranged in an array form such that the each opening of the gate electrodes faces the each cathode electrodes, and the control module determines the dose of X-rays by adjusting the applied voltage between the cathode electrodes and the gate electrodes.

According to another aspect of the present disclosure, a control method of an X-ray source apparatus which emits X-rays to a subject includes: adjusting the dose of X-rays for each position on the subject by performing two-dimensional matrix control to the emitters and the gate electrodes arranged in an array form. Herein, the dose of X-rays for each position on the subject is determined depending on an applied voltage between the cathode electrodes and the gate electrode. Herein, the X-ray source apparatus includes emitters are arranged on an upper surface of a cathode electrode in an array form and the gate electrodes are arranged between the emitters and an anode electrode in an array form such that the each opening of the gate electrodes faces the each cathode electrodes.

According to another aspect of the present disclosure, a fabricating method of an X-ray source apparatus includes: manufacturing multiple emitters by cutting a CNT thin film, a graphene thin film, or a nanocarbon material thin film into a triangle or a quadrangle and processing an end portion of the cut thin film into a point shape or a line shape; combining, with multiple cathode electrodes, one or more of the emitters which have been processed into the point or the line shape; arranging the multiple cathode electrodes combined with the emitters in a two-dimensional array form; forming openings in regions facing the respective cathode electrodes and forming, at the respective openings, gate electrodes combined with a graphene thin film; aligning the gate electrodes and the cathode electrodes arranged in the two-dimensional array form in order for the openings for the respective gate electrodes to face the respective cathode electrodes; and placing an anode electrode in a two-dimensional array at a predetermined distance from the gate electrodes.

According to the present disclosure, two-dimensional matrix control can be performed to the cathode electrodes and the gate electrode, and, thus, it is possible to irradiate X-rays at an optimum dose for each position on the subject. Therefore, it is possible to suppress the irradiation of more X-rays than are needed to the subject. Also, it is possible to obtain a high-resolution and high-quality X-ray image.

As such, according to the present disclosure, two-dimensional matrix control makes it easy to control the dose of X-rays and makes it possible to uniformly irradiate X-rays to the subject. Therefore, it is possible to manufacture a high-resolution surface X-ray source with less dependence on the size of the focus of electron beams.

Further, according to the present disclosure, a CNT thin film is fabricated using only a CNT material without containing an organic material by vacuum filtration and then processed into a point shape or a line shape to manufacture the emitters or a graphene thin film or a nanocarbon material thin film is used to manufacture the emitters. Then, the emitters are arranged in an array form and used as cold cathode electron emitters. Thus, it is possible to generate point or surface electron beams of various sizes. Also, it is possible to adjust the magnitude of current to be emitted. Further, it is possible to manufacture an X-ray source with high transmittance and high density of electron beams.

In the present disclosure, a CNT thin film is used for the emitters instead of a CNT paste cold cathode electron emitters. Therefore, high bonding force in the CNT thin film which is a nanomaterial and high electrical/mechanical adhesion between the CNT emitters and the cathode electrodes can be achieved without using organic material-containing paste or other adhesives. Accordingly, it is possible to overcome a decrease in vacuum level caused by an organic material. Further, it is possible to manufacture an X-ray source with high field emission efficiency and excellent lifetime.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
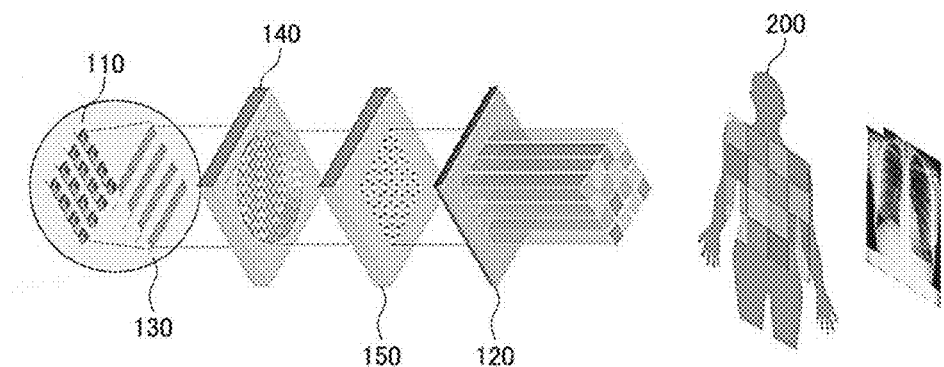
FIG. 1 is a diagram illustrating an X-ray source apparatus in accordance with various embodiments described herein.

Hereinafter, embodiments of the present disclosure will be described in detail with reference to the accompanying drawings so that the present disclosure may be readily implemented by a person with ordinary skill in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added.

Through the whole document, the term "unit" or "module" includes a unit implemented by hardware or software and a unit implemented by both of them. One unit may be implemented by two or more pieces of hardware, and two or more units may be implemented by one piece of hardware.

An embodiment of the present disclosure will be described in detail with reference to the accompanying drawings.

Figure 2:
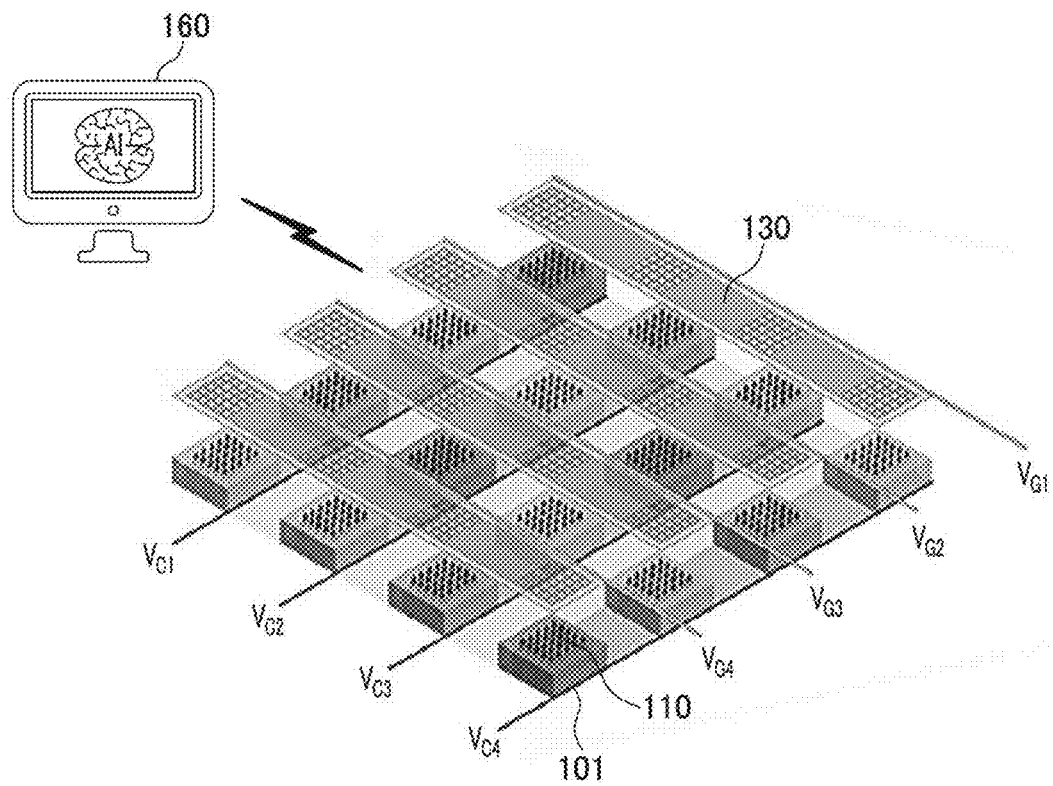
FIG. 2 is a diagram illustrating the X-ray source apparatus capable of performing two-dimensional matrix control in accordance with various embodiments described herein.

FIG. 1 is a diagram illustrating an X-ray source apparatus in accordance with various embodiments described herein, and FIG. 2 is a diagram illustrating the X-ray source apparatus capable of performing two-dimensional matrix control in accordance with various embodiments described herein.

Referring to FIG. 1 and FIG. 2, an X-ray source apparatus 100 configured to emit X-rays to a subject includes a cathode electrode 101, emitters 110, an anode electrode 120, gate electrodes 130, a focusing lens 140, and an electron beam collimator 150.

The cathode electrodes 101, the anode electrode 120, and the gate electrodes 130 may be connected to an external power supply (not illustrated) to apply an electric field. For example, the cathode electrodes 101 may be connected to a negative voltage source or a positive voltage source, and the anode electrode 120 and the gate electrodes 130 may be connected to a voltage source that can apply a higher potential than a potential of the voltage source connected to the cathode electrodes 101.

The emitters 110 are formed on the cathode electrodes 101 and used as cold cathode electron emitters that emits electrons. That is, the emitters 110 may emit electrons using an electric field formed by a voltage applied between the cathode electrodes 101 and the gate electrodes 130. The emitters 110 manufactured using a carbon nanotube (CNT)

thin film can emit point or surface electron beams by processing the CNT thin film into a point shape or a line shape.

Herein, the emitters 110 use the CNT thin film to provide a low threshold field and a high field emission current density, but may also use a graphene thin film or a nanocarbon material thin film (e.g., nanographite thin film, etc.) instead of the CNT thin film to manufacture emitters with high field emission properties.

The anode electrode 120 is provided away from the cathode electrodes 101 at a predetermined distance in an emission direction of an electron beam. The anode electrode may be placed in a two-dimensional array at a predetermined distance from the gate electrodes.

The gate electrodes 130 are positioned between the emitters 110 and the anode electrode 120 and provided away from and above the emitters 110. The gate electrodes 130 are formed by transferring a graphene thin film including at least one or more layers on an upper part of a metal electrode having at least one or more openings.

Further, the gate electrodes 130 may be formed into a metal electrode using a metal plate having a hole or a polygonal metal mesh on which a graphene thin film is attached, in other way, the gate electrodes 130 may be manufactured by inserting a graphene thin film including one or more layers between two metal electrodes. In other words, the gate electrodes 130 combined with a graphene thin film have openings in regions facing the respective cathode electrodes 101 and forming, at the respective openings.

Herein, the gate electrodes 130 and the cathode electrodes 101 may be arranged in the two-dimensional array form in order for the openings for the respective gate electrodes to face the respective cathode electrodes. Therefore, the emitters 110 and the gate electrodes 130 may be arranged in an array form. For example, the multiple emitters 110 spaced in parallel to each other are arranged in parallel in an array form at an equal distance in a first direction and the multiple gate electrodes 130 are arranged in parallel in an array form at an equal distance in a second direction, and the first direction and the second direction may be perpendicular to each other. The focusing lens 140 is positioned between the gate electrodes 130 and the anode electrode 120 and focuses electron beams emitted from the emitters 110 on the anode electrode 120.

The electron beam collimator 150 is positioned between the focusing lens 140 and the anode electrode 120 and enables the electron beams passing through the focusing lens 140 to go straight and be focused on the anode electrode 120. The electron beam collimator 150 can improve the linearity of the electron beams passing through the focusing lens 140.

Meanwhile, as illustrated in FIG. 2, the X-ray source apparatus 100 performs, through a control module 160, two-dimensional matrix control to the emitters 110 and the gate electrodes 130 which are arranged in an array form. Herein, the two-dimensional matrix control is to adjust a voltage level between the emitters 110 and the gate electrodes 130 for each position and thus adjust the generation density of electron beams for each body part. Since the density of X-rays generated by the anode electrode 120 changes as the density of electron beams changes, the two-dimensional matrix control makes it possible to adjust the density of X-rays depending on the bone thickness of each body part.

The control module 160 adjusts the dose of X-rays to be suitable for each position on a subject 200 to generate X-rays. The size of an X-ray source can be adjusted depending on the size of an array, and, thus, a large-scale X-ray source can be implemented.

Meanwhile, the control module 160 may collect characteristics information of the subject 200 such as gender, age, body information, and the like, and locally specify emission information about the dose of X-rays depending on the area to be imaged, the bone position, the bone thickness, and the like on the basis of the collected characteristics information of the subject 200.

For example, since the bone position or the bone thickness distribution is different for each user, a proper local dose of X-rays is set accordingly. To this end, the control module 160 collects characteristics information of the subject 200 such as gender, age, body information (height, weight, body type, etc.), and the like or additional information for identifying each subject and anatomical information of each subject 200 such as the bone position or bone thickness and matches them respectively. If characteristics information of the subject 200 is used, it is possible to estimate anatomical information such as the bone position or bone thickness based on just characteristics information of the subject 200 such as gender, age, body information, and the like and then, it is possible to determine emission information about a proper dose of X-rays for each position based on the estimated anatomical information such as the bone position or bone thickness.

When the emission information about the dose of X-rays for each position is determined, the control module 160 performs two-dimensional matrix control to the emitters 110 and the gate electrodes 130 to perform addressing to the X-ray source apparatus 100 and adjusts voltage levels to be applied to the cathode electrodes 101 and the gate electrodes 130, respectively, to adjust the dose of X-rays from the emitters 110 for each position.

Herein, the control module 160 configured as an intelligent device that supports communication, auto-control, data processing, image data processing, and the like may include all kinds of handheld wireless communication devices, such as a smartphone and a tablet PCT, in which multiple application programs (i.e., applications) desired by a user may be installed and executed or may include wired communication devices, such as a PC, which can access another device or server via a network.

As such, in the X-ray source apparatus 100, the emitters 110 arranged in an array form, the gate electrodes 130 arranged in an array form, the focusing lens 140, the electron beam collimator 150, and the anode electrode 120 are placed sequentially and vacuum packaged within a vacuum container made of any one of a glass material, a ceramic material, or a metal material to implement a cold cathode X-ray source that irradiates X-rays optimized for each position on the subject 200.

Figure 3:
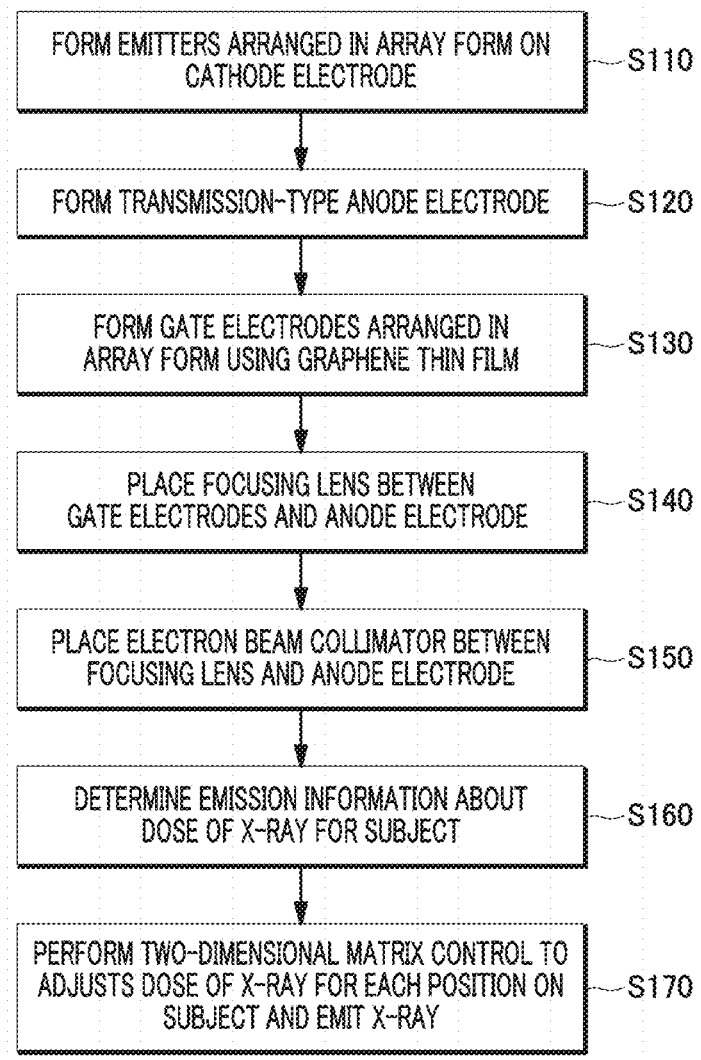
FIG. 3 is a flowchart showing a control method of the X-ray source apparatus in accordance with various embodiments described herein.

FIG. 3 is a flowchart showing a control method of the X-ray source apparatus in accordance with various embodiments described herein.

Referring to FIG. 3, the control method of the X-ray source apparatus is to generate X-rays with an adjusted dose each position on a subject by performing two-dimensional matrix control to emitters and gate electrodes arranged in an array form.

To this end, when emitters without containing an organic material are formed on an upper surface of a cathode electrode by vacuum filtration to emit electrons (S110), the X-ray source apparatus arranges the emitters in an array form in a first direction. Herein, not only CNT emitters manufactured using a CNT thin film but also emitters manufactured using any one of a graphene thin film or a nanocarbon material thin film may be used.

An anode electrode is formed away from the cathode electrodes at a predetermined distance (S120), and gate electrodes are formed using a graphene thin film including at least one or more layers between the emitters and the anode electrode in a second direction perpendicular to the first direction (S130). Herein, the anode electrode is manufactured into a transmission type by depositing a tungsten thin film on a beryllium metal plate. The manufactured transmission-type anode electrode can generate surface X-rays.

A focusing lens provided between the gate electrodes and the anode electrode focuses electron beams emitted from the emitters on the anode electrode (S140) and an electron beam collimator is further provided between the focusing lens and the anode electrode to improve the linearity of the electron beams passing through the focusing lens (S150). Herein, the focusing lens may be manufactured into a general metal electrode with a hole shape or may be manufactured by transferring one or more graphene layers on the hole-shaped metal electrode. Further, one or two focusing lenses may be used.

The X-ray source apparatus includes the emitters and the gate electrodes arranged in an array form to cross perpendicular to each other, and the emitters and the gate electrodes may be a large-size emitter and a large-size gate electrode, respectively, to which two-dimensional matrix control can be performed.

The X-ray source apparatus collects characteristics information of the subject such as gender, age, body information, and the like, and locally specifies emission information about the dose of X-rays depending on the area to be imaged, the bone position, the bone thickness, and the like on the basis of the collected characteristics information of the subject and then outputs the emission information (S160). That is, when the emission information about the dose of X-rays for each position is determined, the X-ray source apparatus performs two-dimensional matrix control to the emitters and the gate electrodes arranged in an array form to perform addressing, adjusts voltage levels to be applied to the cathode electrodes and the gate electrodes, respectively, to adjust the dose of X-rays from the emitters for each position, and emits X-rays (S170).

Figure 4:
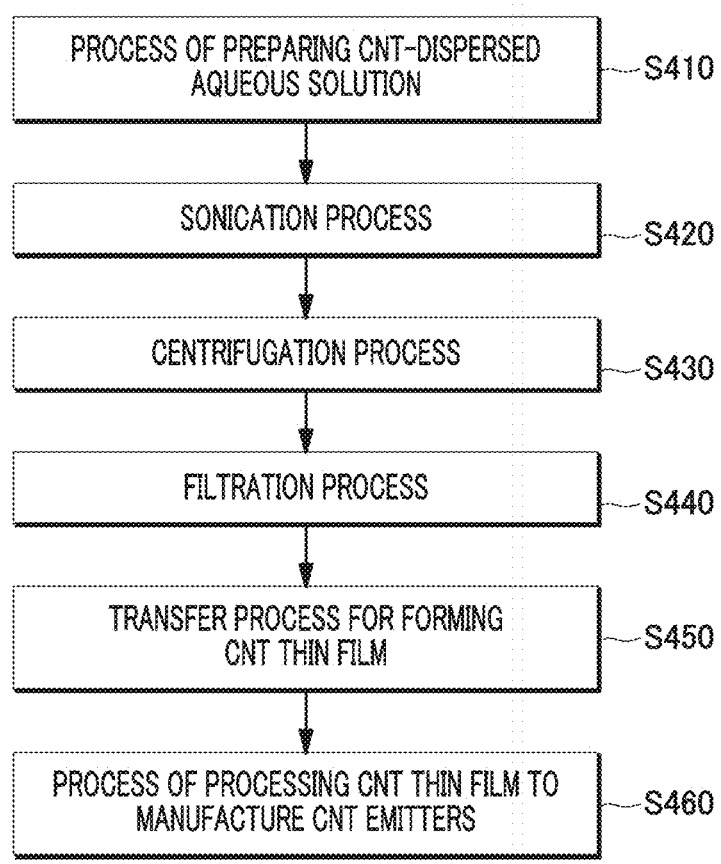
FIG. 4 is a flowchart showing a method of forming CNT emitters illustrated in FIG. 3.
Figure 5:
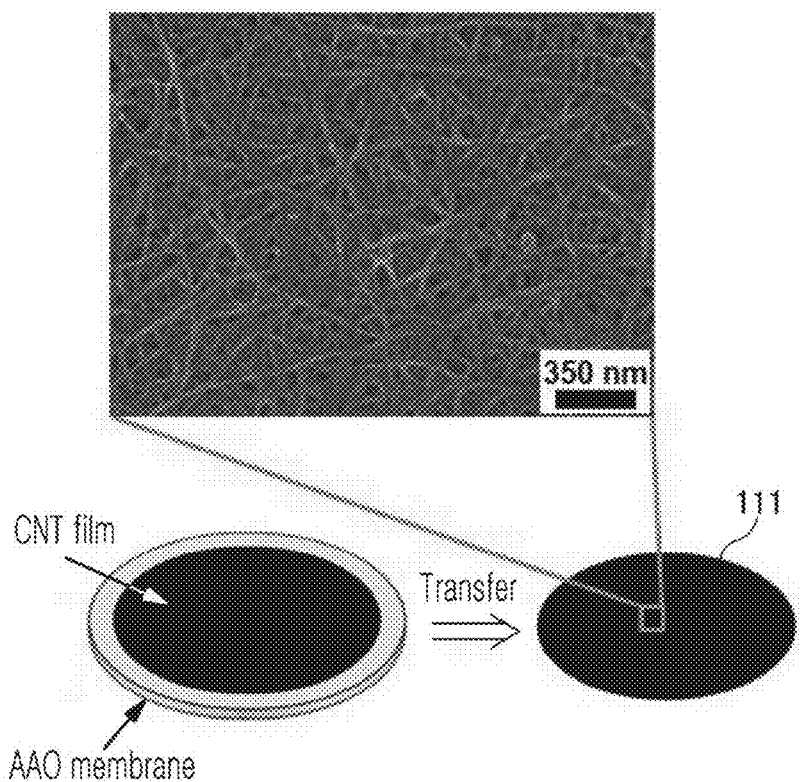
FIG. 5 is a diagram illustrating a CNT thin film including a CNT network therein by the method shown in FIG. 4.
Figure 6:
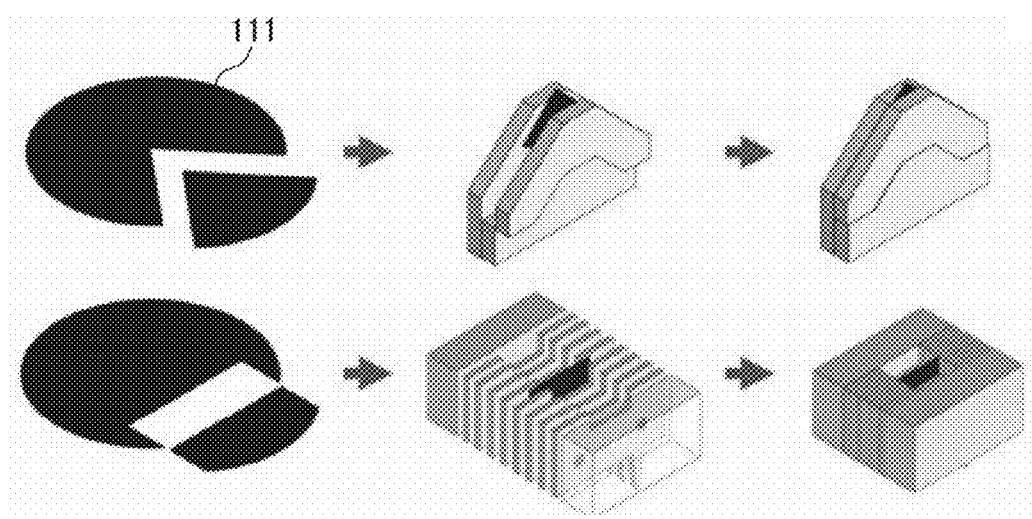
FIG. 6 is a diagram illustrating a CNT thin film processed into a polygonal shape by the method shown in FIG. 4.
Figure 7:
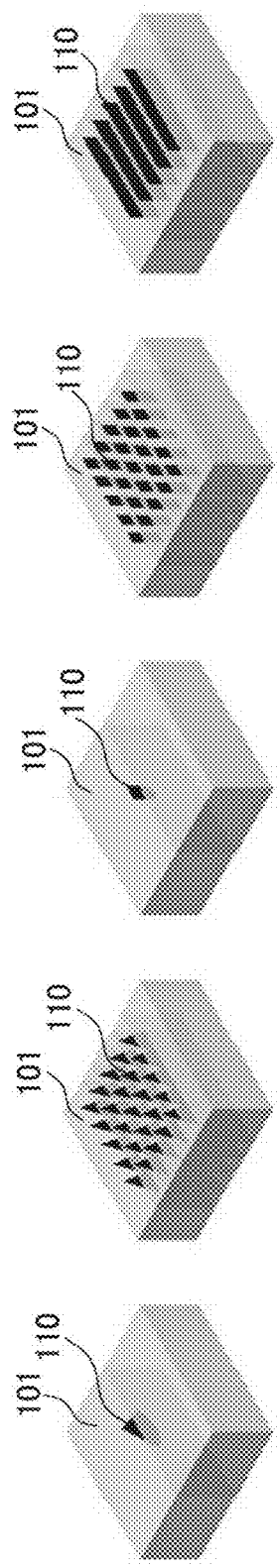
FIG. 7 is a diagram illustrating various examples of the CNT emitters processed into a point or surface shape by the method shown in FIG. 4.
Figure 8:
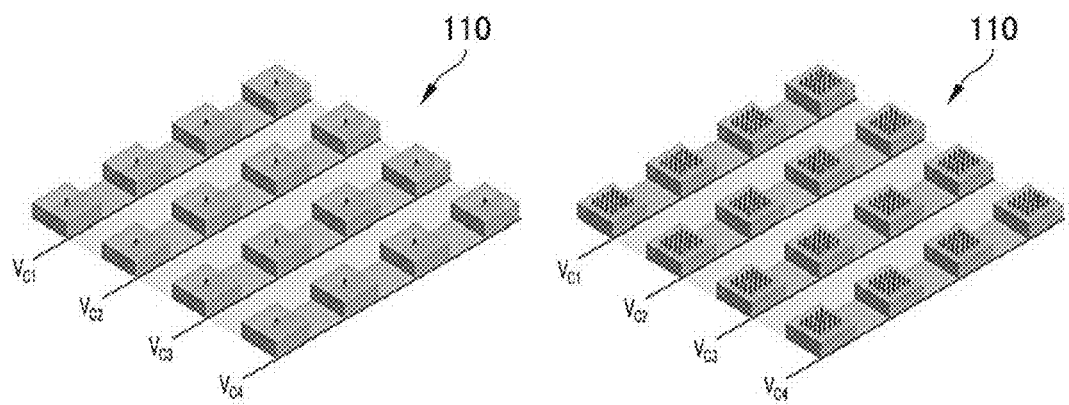
FIG. 8 is a diagram illustrating the arrangement of the CNT emitter array formed by the method shown in FIG. 7.

FIG. 4 is a flowchart showing a method of forming CNT emitters illustrated in FIG. 3, FIG. 5 is a diagram illustrating a CNT thin film including a CNT network therein by the method shown in FIG. 4, and FIG. 6 is a diagram illustrating a CNT thin film processed into a polygonal shape by the method shown in FIG. 4. FIG. 7 is a diagram illustrating various examples of the CNT emitters processed into a point or surface shape by the method shown in FIG. 4, and FIG. 8 is a diagram illustrating the arrangement of the CNT emitter array formed by the method shown in FIG. 7.

Referring to FIG. 4 through FIG. 8, a CNT-dispersed aqueous solution is prepared by dispersing 200 mg of sodium dodecyl sulfate (SDS) and 4 mg of single-walled carbon nanotube in 200 ml of distilled (DI) water (S410). After a sonication process for 65 minutes (S420) and a centrifugation process for 40 minutes (S430), the CNT-dispersed aqueous solution is filtered through an anodic aluminum oxide (AAO) membrane to allow only the DI water to pass through. Then, CNTs remain unfiltered and deposited on the AAO membrane (S440).

As shown in FIG. 5, the CNTs unfiltered on the AAO are strongly entangled to one another by van der Waals forces. Then, when the AAO membrane is dissolved in a sodium hydroxide (NaOH) solution, a CNT thin film including a CNT network therein is prepared (S450). In this case, through a densification process, the CNT thin film is dipped in an isopropyl alcohol solution (IPA) and then dried to make the CNTs more entangled to one another. After the densification process, a scanning electron microscope image shows that the CNT thin film has a densely entangled CNT network.

As shown in FIG. 6, the CNT thin film 111 is cut into a polygonal shape such as a triangle or a quadrangle and pressed into a flat plate to manufacture an electron emitter, and the CNT emitters 110 are formed on an upper surface of the cathode electrodes 101 (S460). Herein, a carbonization process is performed for the CNT emitters 110 to more stably operate. When an organic polymer material, i.e., carbon-based material, is coated on the CNT thin film 111 and annealed at a high temperature in a vacuum through the carbonization process, the carbon-based material is inserted into an empty space between the CNTs in the CNT network. Through this process, the bonding force between the CNTs can be further increased.

As shown in FIG. 7, the CNT thin film may be manufactured into a point- or line-shaped CNT emitters 110 according to the cutting method. If the CNT thin film 111 is cut into a triangular shape, an upper part of the cut portion may converge on a point, and if the CNT thin film 111 is cut into a quadrangular shape, an upper part of the cut portion may converge on a line.

Thus, the processed CNT thin film with the cathode electrodes may be combined N columns of the CNT thin film by combining the processed CNT thin film between N+1 number of cathode electrode blocks which are separated from each other in parallel.

Further, as shown in FIG. 8, if multiple CNT thin films 111 are processed into a point or line shape and then inserted in the cathode electrodes 101 to form the CNT emitters 110 arranged in an array form, the CNT emitters can generate point or two dimensional electron beams of various sizes according to the cutting method of the CNT thin film.

Figure 9:
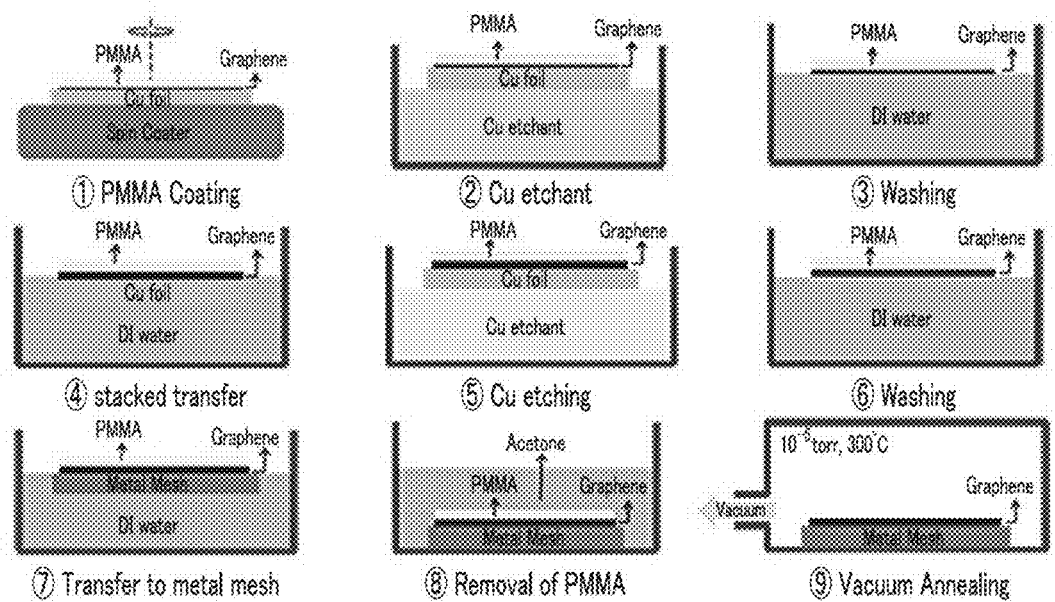
FIG. 9 is a flowchart showing a method of forming gate electrodes illustrated in FIG. 3.
Figure 10:
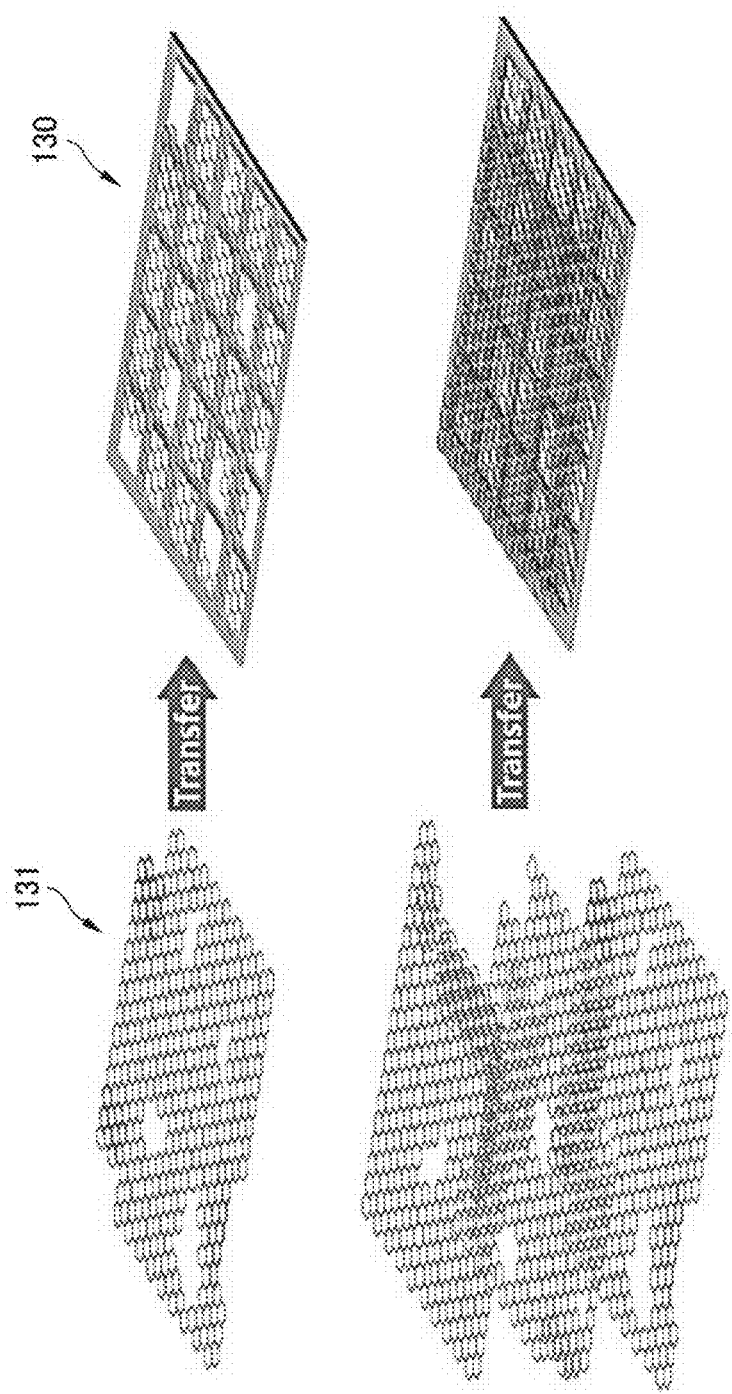
FIG. 10 is a diagram provided to explain a process of transferring a graphene thin film on a metal electrode as illustrated in FIG. 9.
Figure 11:
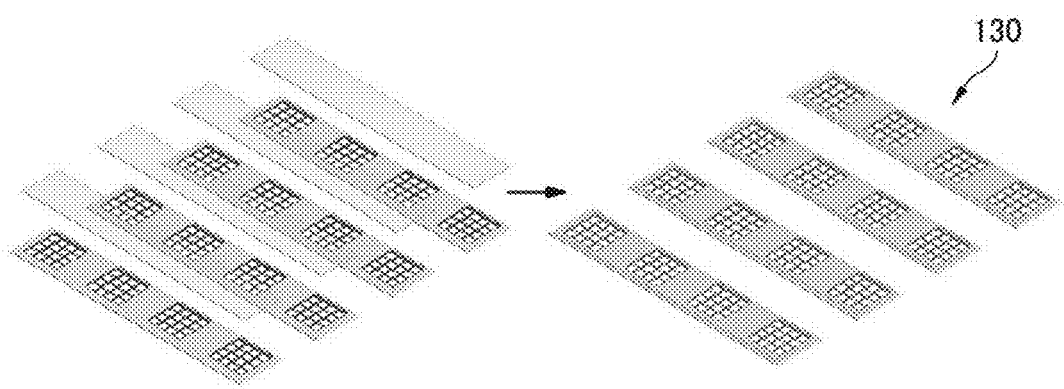
FIG. 11 is a diagram illustrating an example of gate electrodes arranged in an array form by the method shown in FIG. 9.

FIG. 9 is a flowchart showing a method of forming gate electrodes illustrated in FIG. 3, FIG. 10 is a diagram provided to explain a process of transferring a graphene thin film on a metal electrode as illustrated in FIG. 9, and FIG. 11 is a diagram illustrating an example of gate electrodes arranged in an array form by the method shown in FIG. 9.

Referring to FIG. 9 through FIG. 11, the method of forming gate electrodes includes synthesizing graphene on a copper foil by thermal chemical vapor deposition (CVD) and coating polymethylmethacrylate (PMMA) on the graphene with a spin coater (①).

Then, the copper foil is removed using a copper etching solution (②), followed by washing with DI water to remove the remaining copper foil (③). By repeating this process several times, a graphene thin film including multiple laminated layers is prepared. Then, as shown in FIG. 10, a graphene thin film including one or more layers is transferred onto a metal electrode (④, ⑤, ⑥, ⑦). In this case, the metal electrode may be a metal plate having circular holes or a metal mesh having a quadrangular, circular, or hexagonal shape.

The graphene thin film 131 is transferred onto the metal electrode and then dipped in an acetone solution and dried to remove the PMMA remaining on the graphene thin film 131 and annealed at 300° C. in a vacuum atmosphere of $10^{-5}$ Torr or less to manufacture the gate electrodes 130 on which the graphene thin film is stably transferred (⑧, ⑨). Further, as shown in FIG. 11, the gate electrodes 130 arranged in an array form may be manufactured into a large-size gate electrode, in which the two-dimensional matrix control can be performed. Herein, the gate electrodes may be manufactured by inserting a graphene thin film including one or more layers between two metal electrodes.

So, the gate electrodes may be formed, in main bodies of the gate electrodes, the openings in the regions facing the respective cathode electrodes. And, the gate electrodes may be transferred a graphene thin film on the main bodies of the gate electrodes including the openings, and annealed the main bodies of the gate electrodes on which the graphene thin film has been transferred.

The gate electrodes manufactured using the graphene thin film including at least one layer can uniformly apply an electric field, and, thus, the linearity of electron beams can be improved. Further, the graphene is an atomic scale mesh, and, thus, the transmission efficiency of electron beams can be increased. Furthermore, due to the graphene with very high heat transfer efficiency, heat caused by the collision of electron beams can be effectively dispersed, and, thus, the thermal stability of the gate electrodes can be improved.

Meanwhile, similar to the gate electrodes, the focusing lens may be manufactured by transferring graphene including one or more layers onto a metal plate or a metal mesh or inserting at least one graphene thin film into two focusing lens.

As described above, the X-ray source apparatus and the control method thereof according to an embodiment of the present disclosure uses cold cathode electron emitters using a CNT thin film and can irradiate X-rays with a two-dimensional area to a subject through a transmission-type anode electrode and drive electron beams generated from the CNT emitters by matrix control to irradiate X-rays at an optimum dose for each position on the subject.

The control method of the above-described X-ray source apparatus according to the embodiments of the present disclosure can be embodied in a storage medium including instruction codes executable by a computer such as a program module executed by the computer. The storage medium includes a computer-readable medium, and the computer-readable medium can be any usable medium which can be accessed by the computer and includes all volatile/non-volatile and removable/non-removable media. Further, the computer-readable medium may include all computer storage media. The computer storage media include all volatile/non-volatile and removable/non-removable media embodied by a certain method or technology for storing information such as computer-readable instruction code, a data structure, a program module or other data.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

Further, the method and system of the present disclosure have been explained in relation to a specific embodiment, but their components or a part or all of their operations can be embodied by using a computer system having general-purpose hardware architecture.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. An X-ray source apparatus that emits X-rays to a subject, comprising:
   a plurality of cathode electrodes having a plurality of emitters formed on an upper surface of plurality of cathode electrodes;
   an anode electrode arranged at a predetermined distance from the plurality of cathode electrodes;
   a plurality of gate electrodes positioned between the plurality of emitters and the anode electrode, wherein each gate electrode of plurality of gate electrodes is formed by transferring a graphene thin film on a metal electrode having at least one or more openings;
   a focusing lens positioned between the plurality of gate electrodes and the anode electrode and configured to focus electron beams emitted from the plurality of emitters on the anode electrode; and
   a control module configured to adjust dose of X-rays for each position on the subject by performing two-dimensional matrix control to the plurality of emitters and the plurality of gate electrodes,
   wherein
      the plurality of cathode electrodes are arranged in an array form, the gate electrodes are arranged in an array form such that the each opening of the plurality of gate electrodes faces the each cathode electrode of the plurality of cathode electrodes,
      the control module is configured determine the dose of X-rays by adjusting a voltage between the cathode electrodes and the gate electrodes, and
      the control module performs two-dimensional matrix control to adjust a voltage level between the emitters and the gate electrodes and thus adjust generation density of electron beams for each subject part.

2. The X-ray source apparatus of claim 1, further comprising:
   an electron beam collimator positioned between the focusing lens and the anode electrode and configured to allow the electron beams passing through the focusing lens to go straight and be focused on the anode electrode.

3. The X-ray source apparatus of claim 1, wherein
   the plurality of emitters are formed using a carbon nanotube (CNT) thin film which is formed by vacuum filtration, and
   the CNT thin film is formed by a densification process using an alcohol solution or a carbonation process in which an organic polymer material is coated and then annealed at a high temperature in a vacuum.

4. The X-ray source apparatus of claim 3, wherein
   the plurality of emitters are formed by processing the CNT thin film into a point shape or a line shape, and
   at least one CNT thin film, which is cut into a point shape or a line shape, is pressed into a flat metal plates and then inserted in the plurality of cathode electrodes.

5. The X-ray source apparatus of claim 1,
   wherein the plurality of gate electrodes comprises two metal electrodes and at least one graphene thin film inserted in the two metal electrodes.

6. The X-ray source apparatus of claim 1,
   wherein the focusing lens is manufactured into a hole shape or manufactured by transferring at least one graphene thin film onto the hole shape.

7. The X-ray source apparatus of claim 1,
wherein the emitters are formed using any one of a carbon nanotube (CNT) thin film, a graphene thin film, or a nanocarbon thin film.

8. The X-ray source apparatus of claim 1,
wherein the plurality of emitters, the plurality of gate electrodes, the focusing lens, and the anode electrode are placed sequentially within a vacuum container made of any one of a glass material, a ceramic material, or a metal material.

9. The X-ray source apparatus of claim 2,
wherein the plurality of emitters, the plurality of gate electrodes, the focusing lens, the electron beam collimator, and the anode electrode are placed sequentially within a vacuum container made of any one of a glass material, a ceramic material, or a metal material, and the dose of X-rays by adjusting a voltage between the emitters and the gate electrodes.

10. A control method of an X-ray source apparatus which emits X-rays to a subject, comprising:
adjusting dose of X-rays for each position on the subject by performing two-dimensional matrix control to a plurality of emitters and a plurality of gate electrodes arranged in an array form,
wherein in the X-ray source apparatus includes:
the emitters arranged on an upper surface of a plurality of cathode electrodes in an array form and
the plurality of gate electrodes arranged between the plurality of emitters and an anode electrode in an array form such that each opening of the plurality of gate electrodes faces the each cathode electrode of the plurality of cathode electrodes,
wherein each gate electrode of plurality of gate electrodes is formed by transferring a graphene thin film on a metal electrode having at least one or more openings,
wherein the dose of X-rays for each position on the subject is determined by adjusting a voltage between the cathode electrodes and the gate electrodes, and
wherein the control module
performs two-dimensional matrix control to adjust a voltage level between the emitters and the gate electrodes, and
adjusts generation density of electron beams for each subject part.

11. The control method of an X-ray source apparatus of claim 10,
wherein the plurality of emitters are point-shaped or line-shaped electron emitters formed by cutting any one of a carbon nanotube (CNT) thin film, a graphene thin film, or a nanocarbon thin film into a point shape or a line shape and pressing the cut thin film into a flat plate.

12. The control method of an X-ray source apparatus of claim 10,
wherein the plurality of emitters, the plurality of gate electrodes, the focusing lens, and the anode electrode are placed sequentially within a vacuum container made of any one of a glass material, a ceramic material, or a metal material.

13. The control method of an X-ray source apparatus of claim 10, wherein the X-ray source apparatus further comprises
an electron beam collimator positioned between the focusing lens and the anode electrode and configured to allow the electron beams passing through the focusing lens to go straight and be focused on the anode electrode, and
the plurality of emitters, the plurality of gate electrodes, the focusing lens, the electron beam collimator, and the anode electrode are placed sequentially within a vacuum container made of any one of a glass material, a ceramic material, or a metal material.

14. A fabricating method of an X-ray source apparatus, the fabricating method comprising:
forming a plurality of emitters by cutting a carbon nanotube (CNT) thin film, a graphene thin film, or a nanocarbon material thin film into a triangle or a quadrangle and processing an end portion of the cut thin film into a point shape or a line shape;
combining, with a plurality of cathode electrodes, one or more of the plurality of emitters which have been processed into the point shape or the line shape;
arranging the plurality of cathode electrodes combined with the plurality of emitters in a two-dimensional array form;
forming openings in regions facing the respective cathode electrodes and forming, at the respective openings, a plurality of gate electrodes combined with a graphene thin film;
aligning the plurality of gate electrodes and the plurality of cathode electrodes arranged in the two-dimensional array form in order for the openings for the respective gate electrodes to face the respective cathode electrodes; and
placing an anode electrode in a two-dimensional array at a predetermined distance from the plurality of gate electrodes,
wherein the combining of the plurality of emitters with the plurality of cathode electrodes includes:
combining N columns of emitter groups each containing one or more emitters between N+1 number of cathode electrode blocks which are separated from each other in parallel.

15. The fabricating method of an X-ray source apparatus of claim 14, further comprising:
placing
a focusing lens which is positioned between the cathode electrodes and the anode electrode and configured to focus electron beams emitted from the plurality of emitters on the anode electrode and
an electron beam collimator which is positioned between the focusing lens and the anode electrode and configured to allow the electron beams passing through the focusing lens to go straight and be focused on the anode electrode.

16. The fabricating method of an X-ray source apparatus of claim 14, wherein the forming of the gate electrodes includes:
forming, in main bodies of the plurality of gate electrodes, the openings in the regions facing the respective cathode electrodes;
transferring a graphene thin film on the main bodies of the plurality of gate electrodes including the openings; and
annealing the main bodies of the plurality of gate electrodes on which the graphene thin film has been transferred.

* * * * *